United States Patent [19]

Klemann et al.

[11] Patent Number: 5,008,126

[45] Date of Patent: Apr. 16, 1991

[54] LONG CHAIN DIOL DIESTERS AS LOW CALORIE FAT MIMETICS

[75] Inventors: Lawrence P. Klemann, Somerville; John W. Finley, Whippany; Anthony Scimone, Cedar Grove, all of N.J.

[73] Assignee: Nabisco Brands, Inc., East Hanover, N.J.

[21] Appl. No.: 372,056

[22] Filed: Jun. 27, 1989

[51] Int. Cl.$^5$ .............................................. A23D 7/00
[52] U.S. Cl. .................................. 426/611; 426/601; 426/604; 426/804; 260/410.6; 560/263; 560/262
[58] Field of Search ............... 426/601, 604, 611, 804; 250/410.6; 560/263, 262

[56] References Cited

U.S. PATENT DOCUMENTS

| | | | |
|---|---|---|---|
| 519,980 | 5/1894 | Winter . | |
| 2,962,419 | 11/1960 | Minich | 167/81 |
| 2,993,063 | 7/1961 | Alsop et al. | 260/410.6 |
| 3,495,010 | 2/1970 | Fossel | 424/312 |
| 3,579,548 | 5/1971 | Whyte | 260/410.7 |
| 3,600,186 | 8/1971 | Mattson et al. | 99/1 |
| 3,637,774 | 1/1972 | Babayan et al. | 260/410.6 |
| 3,651,102 | 3/1972 | Coopersmith | 560/263 |
| 3,818,089 | 6/1974 | Bayley et al. | 424/9 |
| 3,876,794 | 4/1975 | Rennhard | 426/152 |
| 4,005,195 | 1/1977 | Jandacek | 424/180 |
| 4,304,768 | 12/1981 | Staub et al. | 424/180 |
| 4,314,947 | 2/1982 | Hohenschutz et al. | 560/263 |
| 4,508,746 | 4/1985 | Hamm | 426/601 |
| 4,631,196 | 12/1986 | Zeller | 426/580 |

FOREIGN PATENT DOCUMENTS

| | | |
|---|---|---|
| 1106681 | 8/1981 | Canada . |
| 205273 | 12/1986 | European Pat. Off. . |
| 233856 | 8/1987 | European Pat. Off. . |
| 254547 | 1/1988 | European Pat. Off. . |
| 652329 | 3/1951 | United Kingdom ............ 560/263 |

OTHER PUBLICATIONS

Nikkari et al., "Isolation and Analysis of Two Types of Diester Waxes from the Skin Surface Lipids of the Rat", Biochimica et Biophysica Acta, vol. 164, 1968, pp. 294–305.

Okumura et al., "Synthesis of Various Kinds of Esters by Four Microbial Lipases", Biochimica et Biophysica Acta, vol. 575, 1979, pp. 156–165.

Bergelson, L. D. et al., 116 B.B.A. 511–520, (1966).

Booth, A. N., and Gros, A. T., 40 J.A.O.C.S. 551–553, (1963).

Brind, J. L., et al., 84B Comp. Biochem. Physiol. 403–407, (1986).

Goodman & Gilman's Pharmacological Basis of Therapeutics, 7th ed., Macmillan, 1002–1003, (1985).

Gurr, M. I., and James, A. T., Lipid Biochemistry, 3rd ed., Chapman Hall, 90–92, (1980).

Halliburton, W. D., et al., 13, J.B.C. 301–305, (1919).

Hamm, D. J., 49 J. Food Sci. 419–428, (1984).

Haumann, B. J., 63 J.A.O.C.S. 278–287, (1986).

LaBarge, R. G., 42 Food Tech. 84–90, (1988).

Lapworth, A., and Pearson, L. K. 13 J.B.C. 296–300, (1919).

Markley, K. S., ed., Fatty Acids, 2d ed., part 2, Krieger, 785–797, (1983).

Marosi, L., and Schlenk, W., 1973, Liebigs Ann. Chem. 584–598, English Abstract.

Smith, E., et al., Principles of Biochemistry, 7th ed., McGraw-Hill, 117, (1983).

Stryker, W. A., 31 Arch. Path. 670, (1941).

Iwai, M., and Tsujisaka, Y., in Borgstroem and Brockman's Lipases, Elsevier, New York, 1987, pp. 457–462.

Zaks, A. and Klibanov, A. M., 82 P.N.A.S. U.S.A. 3192–3196, (1985).

*Primary Examiner*—Donald E. Czaja
*Assistant Examiner*—Evan Federman

[57] ABSTRACT

Long chain diol diesters, notably 11- to 30- carbon aliphatic chains having two vicinal fatty acid esters or dicarboxylate-extended fatty acid esters, or two fatty acid esters of dicarboxylate-extended fatty acid esters separated by one or two methylene groups, attached to one end of the chain, are edible, preferably partially digestible, fat replacements for foods.

54 Claims, No Drawings

LONG CHAIN DIOL DIESTERS AS LOW CALORIE FAT MIMETICS

BACKGROUND OF THE INVENTION

This invention relates to the use of long chain diol diesters, notably aliphatic chains of 11 to 30 carbons having two fatty acid esters or two dicarboxylate-extended fatty acid esters, or two fatty acid esters or two dicarboxylate-extended fatty acid esters, as substitutents separated by one or two methylene groups and attached to one end of the chain, as edible, preferably partially digestible, fat replacements for foods and pharmaceuticals.

Since fats provide nine calories per gram compared to four calories per gram provided by protein or carbohydrates, major research efforts toward reduction of caloric intake for medical or health reasons have focused on ways to produce food substances that provide the same functional and organoleptic properties as fats, but not the calories.

A major strategy for developing low calorie replacement fats has been to structurally re-engineer natural triglycerides in such a way as to retain their conventional functional properties in foods, while removing their susceptibility toward hydrolysis or subsequent absorption during digestion. To this end, the the fatty acids attached to glycerol have been replaced with alternate acids (U.S. Pat. No. 3,579,548 to Whyte); groups have been inserted between the fatty acids and the glycerol backbone ("propoxylated glycerols", Eur. Pat. Ap. No. 254,547 to White and Pollard); the ester linkages have been replaced by ether linkages (U.S. Pat. No. 3,818,089 to Bayley and Carlson, and Can. Pat. No. 1,106,681 to Trost); the ester linkages have been reversed (U.S. Pat. No. 4,508,746 to Hamm); and the glycerol moeity has been replaced with an alternate alcohol (e.g., ethylene glycol in U.S. Pat. No. 2,924,528 to Barskey et al., and U.S. Pat. No. 2,993,063 to Alsop and Carr).

A second major approach to the development of a low calorie fat replacement has been to explore or synthesize nonabsorbable polymeric materials structurally unlike triglycerides, but having physical properties similar to edible fat. Mineral oil was disclosed as early as 1894 (U.S. Pat. No. 519,980 to Winter), and, more recently, polydextrose (U.S. Pat. No. 4,631,196 to Zeller), polyglucose and polymaltose (U.S. Pat. No. 3,876,794 to Rennhard), polysiloxane (Eur. Pat. Ap. No. 205,273 to Frye), jojoba wax (W. Ger. Pat. No. 3,529,564 to Anika), and polyethylene polymers (E. Ger. Pat. No. 207,070 to Mieth, et al.) have been suggested.

A third major strategy combines the first two. Rather than restructure triglyceride molecules or find a substitute structurally very dissimilar, this approach explores the use of various polyol esters, compounds which have numbers of fatty acid groups in excess of the three in conventional fat triglycerides, as nonabsorbable fat replacements. Fully esterified sugar alcohols were suggested as fat replacements during World War I (notably mannitol, Lapworth, A., and Pearson, L. K., and Halliburton, W. D., et al., 13 *J. Biol. Chem.* 296 and 301 (1919)); Minich suggested esterifying pentaerythritol, a tetrahydric neopentyl sugar alcohol which can be formed from pentaerythrose, in 1960 (U.S. Pat. No. 2,962,419); and the Southern and Western Regional Research Laboratories of the U.S.D.A. investigated the feasibility of using amylose esters as new-type fats during the 1960's (see Booth, A. N., and Gros, A. T., 40 *J. Amer. Oil Chem. Soc.* 551 (1963) and the references cited therein). More recently, sucrose polyesters have been suggested (U.S. Pat. No. 3,600,186 to Mattson and Volpenhein). The caloric availability and digestibility of a series of dimeric and polymeric glycerides including diglyceride esters of succinic, fumaric, and adipic acids, and polymeric fats from stearic, oleic and short-chain dibasic acids were assessed by the U.S.D.A. group cited supra, and polyglycerol esters have since been suggested (U.S. Pat. No. 3,637,774 to Babayan and Lehman).

Nondigestible or nonabsorbable triglyceride analogues, polyol esters, and polymeric materials have proved disappointing as fat replacements when tested in feeding trials, where gastrointestinal side effects occurred, in some cases so extreme that frank anal leakage was observed (for recent reviews, see Hamm, D. J., 49 *J. Food Sci.* 419 (1984), Haumann, B. J., 63 *J. Amer. Oil Chem. Soc.* 278 (1986), and LaBarge, R. G., 42 *Food Tech.* 84 (1988)). Nondigestible fats act as a laxative and are expelled from the body, eliciting foreign body reactions like those early documented for mineral oil (Stryker, W. A., 31 *Arch. Path.* 670 (1941), more recently summarized in Goodman and Gilman's *Pharmacological Basis of Therapeutics*, 7th ed., Macmillan Pub. Co., N.Y. 1985, pages 1002-1003). Polyglycerol and polyglycerol esters, for example, suggested as fat replacements supra, have been suggested for use as fecal softening agents as well (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, or incorporating saturated fatty groups, Eur. Pat. Ap. No. 233,856 to Bernhardt), and dietary fiber preparations have been incorporated into polysaccharide and/or polyol-containing foodstuffs to help inhibit the diarrheal effect (U.S. Pat. No. 4,304,768 to Staub et al.).

SUMMARY OF THE INVENTION

An object of the present invention is to provide a fat mimetic having substantially fewer calories than normal fat. It is another object of the present invention to provide a fat replacement more compatible with normal digestion, thus minimizing or avoiding laxative side effects. In the preferred embodiment of this invention, it is a further object of the present invention to provide a partially digestible fat replacement which may, if desired, be engineered to provide essential or desirable fatty acids.

In the practice of this invention, long chain diol diesters, notably aliphatic chains having 11 to 30 carbon atoms to which are attached two vicinal fatty acid ester or dicarboxylate-extended fatty acid ester groups, or two fatty acid ester or dicarboxylate-extended ester groups separated by one or two methylene groups at one end of the chain, comprise a new class of edible, preferably partially digestible, fat replacements for food and pharmaceuticals.

DETAILED DESCRIPTION OF THE INVENTION

Although most lipids are derivatives of glycerol, many organisms of animal, plant and microbial origin also contain small amounts of lipids that are derivatives of diols. These include mono- and diacyl esters and mixed alkyl and alkenyl ester fatty acid derivatives of ethylene glycol, 1,2- and 1,3-propanediols, 1,3- 1,4- and 2,3-butanediols, and 1,5-pentanediol isolated from such widely differing tissues as mutton fat, fish liver, egg yolks, corn seeds, yeast and rat liver (Gurr, M. I., and James, A. T., *Lipid Biochemistry*, 3rd ed., Chapman and Hall, New York, 1980, pp. 91–92). These lipids, first separated from neutral lipid components using high-temperature gas-liquid chromatography, were named "diol lipids" (Bergelson, L. D., et al. 116 *Biochem. Biophys. Acta* 11 (1966)). Diol lipids have since been discovered among the ionic lipids, and generally comprise a concentration of 0.5 to 1.5% that of glycerol derivatives (Smith, E. L., et al., *Principles of Biochemistry: General Aspects*, 7th ed., McGraw-Hill, New York, 1983, p. 117), though skin surface lipids can contain much higher concentrations (25–30% and above; see Nikkari, T., an Haahti, E., 164 *Biochim. Biophys. Acta* 294 (1968) and Brind, J. L., et al. 84B *Comp. Biochem. Physiol.* 403 (1986)).

Diol lipids have not figured into the reported fat replacement research which has focused, instead, on ways of providing edible fat replacements for triglycerides. This invention is based on the finding that certain long chain diol diesters which are analogues of both diol lipids, a minor component of natural fat, and triglycerides, the major component, and combine the features of both components, comprise a new class of fat mimetics suitable for use in foods and pharmaceuticals.

The compounds of the present invention can be defined by the following structural formula:

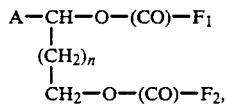

where

A is an alkyl group having from 7 to 28 carbons, n is 0 to 2, and $F_1$ and $F_2$ are aliphatic groups having 1 to 30 carbons or dicarboxylate-extended aliphatic groups of the formula $-(CH_2)_m-(CO)-O-R$, where $m=1$ to 4, and R contains 1 to 30 carbons.

The compounds of this invention have two vicinal fatty groups $F_1$ and $F_2$, either aliphatic groups or dicarboxylate-extended aliphatic groups, separated by one or two (n in the above formula) methylene groups. In compounds having simple fatty acid esters, the compounds are analogues of natural diol lipids, except that the compounds further have an alkyl group, A, having as few as 7 and as many as 28 carbon atoms. In this respect, this class of compounds are also analogues of natural triglycerides, with an end fatty acid ester group replaced by an alkyl group. While not wishing to be bound to any theory, it is believed that this combination of features enable the compounds of this invention to be well suited as fat mimetics.

This invention comprises long chain diol diesters. By "long chain" is meant aliphatic diol esters having 11 to 30, more narrowly 11 to 20, carbons attached to one another by single, double, or triple bonds. Examples of diols which may form the compound backbones are saturated or unsaturated undecanediols, dodecanediols, tridecanediols, tetradecanediols, pentadecanediols, hexadecanediols, heptadecanediols, octadecanediols, nonadecanediols, icosanediols, montanediols, and the like. Chemical formulae and descriptions include isomeric variations. The diols may be normal, iso and neo, having primary, secondary and tertiary hydroxyl groups.

Attached in ester linkage to the diols comprising the compound backbones of this invention are two fatty acid residues in ester linkage or dicarboxylate-extended ester linkage. The term "fatty acid" used here means organic fatty acids of the formula RCOOH having 2 to 31 carbon atoms. The fatty acids may be synthetic or natural, saturated or unsaturated, with straight or branched chains. Examples of fatty acids that can be used in this invention are acetic, propionic, butyric, caproic, caprylic, pelargonic, capric, lauric, undecanoic, myristic, palmitic, stearic, arachidic, behenic, oleic, linoleic, linolenic, eleostearic, and arachidonic acids. Mixtures of fatty acids may be used, such as those obtained from non-hydrogenated or hydrogenated soybean, safflower, sunflower, sesame, peanut, corn, olive, rice bran, canola, babassu nut, coconut, palm kernel, cottonseed, palm, or butter oils. Specific fractions of natural or processed oils may also be used. Halogenated fatty acid derivatives may also be used, such as brominated fatty acids.

Alternatively, $F_1$ and $F_2$ attached to the diol may be dicarboxylate-extended fatty groups. By "dicarboxylate-extended" or "dicarboxylic acid-extended" fatty groups is meant groups formed from the reaction of fatty alcohols (ROH using the nomenclature of the formula above, where R is an an aliphatic group having 1 to 30 carbons) with dicarboxylic acids, such as, for example, malonic, succinic, glutaric or adipic acid, to yield $-(CH_2)_m-(CO)-O-R$, where $m=1$ to 4. These resulting malonyl, succinyl, glutaryl or adipoyl fatty groups are, structurally, aliphatic fatty alcohols with their chains extended by the radicals $-OC-CH_2-CO-$ (malonyl), $-OC-(CH_2)_2-CO-$ (succinyl), $-OC-(CH_2)_3-CO-$ (glutaryl), $-OC-(CH_2)_4-CO-$ (adipoyl), and the like. Thus, where a fatty alcohol is denoted by ROH, a malonyl- (or malonate-extended) fatty group would be $R-O-(CO)-CH_2-(CO)-$, a succinyl- (or succinate-extended) fatty group would be $R-O-(CO)-(CH_2)_2-(CO)-$, a glutaryl- (or glutarate-extended) fatty group would be $R-O-(CO)-(CH_2)_3-(CO)-$, and so forth.

At least one $F_1$ will have 8 or more carbons, and the remainder will be selected to provide a discernible fatty character in the compounds. Many of the F groups will have 3 or more carbon atoms, with a percentage containing 3 to 23, more narrowly 10 to 20, and even more narrowly, 15 to 18 carbon atoms. Where the fatty groups are fatty acid or alcohol groups derived from natural oils, for example, safflower, sunflower, corn or soybean oil, 98% or more of the groups are derived from fatty acids containing 16 to 18 carbon atoms, with 80% or more containing 18 carbon atoms.

The ester groups or dicarboxylate-extended ester groups are attached to one end or terminus, as described in the generalized formula, supra, either in vicinal relation to one another, or separated by one or two methylene groups. In these positions, the diol can be said to be "terminally esterified."

The preferred long chain diol diesters of this invention are partially digestible, and providing from about 0.5 to 8.5 kcal/gram, more narrowly 1.0 to 6.0 kcal/gram. In these preferred compounds, the fatty groups show differential reactivity toward enzymatic hydrolysis, so that the compounds become more hydrophilic when catabolized. The cleaved residue can be an essential or nutritionally desirable fatty acid such as linoleic acid. The cleaved residue can also be a fatty acid with preventative or possible curative effects for certain diseases or conditions, such as, for example, a conjugated linoleic acid.

The ester compounds of this invention may be prepared using standard esterification techniques for diols (reviewed in Markley, K. S., *Fatty Acids*, 2nd ed., part 2, Krieger Pub. Co., 1983, pp. 785–797 and used in preparing long chain derivatives by Marosi, L., and Schlenk, W., *Liebigs Ann. Chem.* 1973 584). These include reactions of the fatty acids, acid chlorides or anhydrides with the diols, or transesterification between fatty acid esters (e.g., fatty acid methyl esters) and alcohols.

The dicarboxylate-extended fatty acid diester compounds of this invention may be prepared by reacting the fatty alcohols or fatty alcohol derivatives with the dicarboxylic acids, and then reacting the fatty acid-dicarboxylic acid adducts with the diols.

A solvent may be employed in the syntheses. The term "solvent" means any material, including the reactants, that is liquid at the synthesis reaction temperature and pressure and will dissolve, suspend or hold the reactants in the reaction mixture in an amount effective to expedite contact for the desired esterification reaction to occur.

The long chain diol esters of this invention may be incorporated either alone, or in combination with another fat (for example, admixed with a triglyceride oil) and/or fat mimetic, into any food composition or used in conjunction with any edible material. The term "edible material" is broad and includes anything edible. Representative of edible materials which can contain the long chain diol diesters of this invention in full or partial replacement of natural fat are: frozen desserts, e.g., sherbet, ice cream, ices, or milk shakes; puddings and pie fillings; margarine substitutes or blends; flavored bread or biscuit spreads; mayonnaise; salad dressings; filled dairy products such as filled cream or filled milk; dairy or non-dairy cheese spreads; coffee lighteners, liquid and dried; flavored dips; frying fats and oils; reformed and comminuted meats; meat substitutes or extenders; whipped toppings; compound coatings; frostings and fillings; cocoa butter replacements or blends; candy, especially fatty candies such as those containing peanut butter or chocolate; chewing gum; bakery products, e.g., cakes, breads, rolls, pastries, cookies, biscuits, and savory crackers; mixes or ingredient premixes for any of these; as well as flavor, nutrient, drug or functional additive delivery systems.

The following is a list of representative, but not limiting, examples of long chain diol lipids of this invention:

(A) Diol diesters with vicinal groups at the terminus of an aliphatic chain having the general formula:

$$\begin{array}{l} A-CH-O-(CO)-F_1 \\ \phantom{A-}|\\ \phantom{A-}CH_2-O-(CO)-F_2. \end{array}$$

where

A is an aliphatic chain having 9 to 28 carbons, and $F_1$ and $F_2$ are aliphatic groups having 1 to 30 carbon atoms, or carboxylate-extended groups of the formula $-(CH_2)_m-(CO)-O-R$, with $m=1$ to 4, and R having 1 to 30 carbon atoms.

Examples of this type of long chain diol esters include (1) 1,2-Dodecane Dioleate
$H_2C-O-(CO)-(CH_2)_7CH=CH(CH_2)_7CH_3$
$HC-O-(CO)-(CH_2)_7CH=CH(CH_2)_7CH_3$
$(CH_2)_9CH_3$ (2) Tetradecane 1-Myristate-2-palmitate
$H_2C-O-(CO)-(CH_2)_{12}CH_3$
$HC-O-(CO)-(CH_2)_{14}CH_3$
$(CH_2)_9CH_3$ (3) 1,2-Tetradecane Dioleate
$H_2C-O-(CO)-(CH_2)_7CH=CH(CH_2)_7 CH_3$
$HC-O-(CO)-(CH_2)_7CH=CH(CH_2)_7CH_3$
$(CH_2)_{11}CH_3$ (4) 1,2-Tetradecane Di-10-undecenate
$H_2C-O-(CO)-(CH_2)_8CH=CH_2$
$HC-O-(CO)-(CH_2)_8CH=CH_2$
$(CH_2)_{11}CH_3$ (5) Tetradecane 1-Laurate-2-Linoleate
$H_2C-O-(CO)-(CH_2)_{10}CH_3$
$HC-O-(CO)-(CH_2)_7CH=CHCH_2CH=CH(CH_2)_4CH_3$
$(CH_2)_{11}CH_3$ (6) 1,2-Hexadecane Dipalmitate
$H_2C-O-(CO)-(CH_2)_{14}CH_3$
$HC-O-(CO)-(CH_2)_{14}CH_3$
$(CH_2)_{13}CH_3$ (7) 1,2-Octadecane Dioleate
$H_2C-O-(CO)-(CH_2)_7CH=CH(CH_2)_7CH_3$
$HC-O-(CO)-(CH_2)_7CH=CH(CH_2)_7CH_3$
$(CH_2)_{15}CH_3$ (8) Octadecane 1-Linoleate-2-oleate
$H_2C-O-(CO)-(CH_2)_7CH=CHCH_2CH=CH(CH_2)_4CH_3$
$HC-O-(CO)-(CH_2)_7CH=CH(CH_2)_7CH_3$
$(CH_2)_{15}CH_3$ (9) 1,2-Icosane Di-10-undecenate
$H_2C-O-(CO)-(CH_2)_8CH=CH_2$
$HC-O-(CO)-(CH_2)_8CH=CH_2$
$(CH_2)_{17}CH_3$

(10) 1,2-Hexadec-5-ene Dipalmitate
$H_2C-O-(CO)-(CH_2)_{14}CH_3$
$HC-O-(CO)-(CH_2)_{14}CH_3$
$(CH_2)_2CH=CH(CH_2)_9CH_3$

(11) Tetradec-9-ene 1-Oleate-2-myristate
$H_2C-O-(CO)-(CH_2)_7CH=CH(CH_2)_7CH_3$
$HC-O-(CO)-(CH_2)_{12}CH_3$
$(CH_2)_6CH=CH(CH_2)_3CH_3$ -continued

(12) Tetradecane Disuccinyloleate

H₂C—O—(CO)—(CH₂)₂—(CO)—O—(CH₂)₈CH=CH(CH₂)₇CH₃
|
HC—O—(CO)—(CH₂)₂—(CO)—O—(CH₂)₈CH=CH(CH₂)₇CH₃
|
(CH₂)₁₁CH₃

(13) Tetradecane Dibromooleate

H₂C—O—(CO)—(CH₂)₇CHBrCHBr(CH₂)₇CH₃
|
HC—O—(CO)—(CH₂)₇CHBrCHBr(CH₂)₇CH₃
|
(CH₂)₁₁CH₃

(14) 1,2-Tetradecane Dibromo-10-undecenate

H₂C—O—(CO)—(CH₂)₈CHBrCH₂Br
|
HC—O—(CO)—(CH₂)₈CHBrCH₂Br
|
(CH₂)₁₁CH₃

(15) 1,2-Montanyl Dioleate

H₂C—O—(CO)—(CH₂)₇CH=CH(CH₂)₇CH₃
|
HC—O—(CO)—(CH₂)₇CH=CH(CH₂)₇CH₃
|
(CH₂)₂₆CH₃

(B) Diol diesters with the ester groups separated by one or two methylene groups having the general formula:

$$A-CH-O-(CO)-F_1$$
$$|$$
$$(CH_2)_n$$
$$|$$
$$CH_2-O-(CO)-F_2,$$

where
n = 1 or 2,
A is an aliphatic chain having 8 to 27 carbons,
$F_1$ and $F_2$ are aliphatic groups having 1 to 30 carbon atoms,
or carboxylate-extended groups of the formula —(CH₂)$_m$—(CO)—O—R, with m = 1 to 4, and R having 1 to 30 carbon atoms.

Examples of this type of long chain diol diesters include:

(16) 1,3-Tetradecane Dioleate

H₂C—O—(CO)—(CH₂)₇CH=CH(CH₂)₇CH₃
|
CH₂
|
HC—O—(CO)—(CH₂)₇CH=CH(CH₂)₇CH₃
|
(CH₂)₁₀CH₃

(17) Pentadecane 1-Laurate-4-palmitate

H₂C—O—(CO)—(CH₂)₁₀CH₃
|
(CH₂)₂
|
HC—O—(CO)—(CH₂)₁₄CH₃
|
(CH₂)₁₀CH₃

(18) 1,3-Heptadec-7, 12-diene Dioleate

H₂C—O—(CO)—(CH₂)₇CH=CH(CH₂)₇CH₃
|
CH₂
|
HC—O—(CO)—(CH₂)₇CH=CH(CH₂)₇CH₃
|
(CH₂)₃CH=CH(CH₂)₃CH=CH(CH₂)₃CH₃

(19) 1,4-Tetradec-13-ene Di-10-undecenate

H₂C—O—(CO)—(CH₂)₈CH=CH₂
|
(CH₂)₂
|
HC—O—(CO)—(CH₂)₈CH=CH₂
|
(CH₂)₈CH=CH₂

EXAMPLES

The following examples are presented to further illustrate and explain the present invention and should not be taken as limiting in any regard. Unless otherwise indicated, all parts and percentages (in both the chemical syntheses and food recipes) are by weight, and are based on the weight at the particular stage of the processing being described. The proton NMR spectra have assigned chemical shifts, multiplicities, and intensities consistent with the structures for which they are reported.

EXAMPLE 1

1,2 Tetradecane dioleate (also called 1,2-bis (oleoyloxy)tetradecane), a diol lipid analogue of this invention, is prepared in this example.

A 5-liter round bottom flask is charged with 414 grams (1.8 moles) 1,2-tetradecanediol and 1.5 liters pyridine. The flask contents are stirred by means of a mechanical stirrer to produce a solution. To this is added 1260 mL (ca. 3.8 moles) oleoyl chloride in five portions with vigorous stirring. The reaction is exothermic and produces a white precipitate. After cooling at room temperature (1.75 hours), the mixture is suction filtered through a Buchner funnel and the solid pyridinium chloride is washed with three 50-mL portions of hexane. The filtrate is concentrated by means of a vacuum rotary evaporator (ca. 100 torr) at 100° C., and then is suction filtered through 500 grams of chromatographic grade silica.

The filtrate is decolorized with ca. 5 wt. % activated carbon and given a final filtration through 150 grams silica. The resulting oil is diluted with ⅓ volume of hexane and washed with 5% HCl (800 mL), dried over anhydrous sodium sulfate and magnesium sulfate, and finally filtered and concentrated by rotary evaporation. The residue is passed through a falling film still (168° C., ca. 1 torr) and steam deodorized (200° C., 1 torr) with ca. 5 wt. % water to afford 900 grams (67%) of the title composition as a clear, amber colored oil.

Proton NMR Spectrum in CDCl₃: chemical shift in ppm (multiplicity; intensity; assignment): 5.32 (multiplet; 4 H; HC=CH), 5.08 (apparent quartet of doublets J=7.0, 7.0, 6.3 and 4.2 Hz; 1 H; methine proton), 4.22 (doublet of doublets, J=13.0 and 4.2 Hz, 1 H, one half of —CH₂—O), 4.04 (doublet of doublets, J=13.0 and 6.3 Hz, 1 H, one half of —CH₂—O), 2.30 (triplet; 4 H, O=C—CH₂), 2.01 (multliplet; 8 H, C=C—CH₂), 1.60 (broad multiplet, 6 H, O=C—C—CH₂ and O—C—CH₂), 1.30 (multiplet; 60 H, —CH₂—) and 0.87 (triplet, 9 H, —CH₃).

EXAMPLE 2

1,2-Dodecane dioleate (also called 1,2-bis(cis-9-octadecenoyloxy)dodecane, another long chain diol diester of this invention, is prepared in this example.

To a solution of 2.02 g, (0.01 mole) dodecane-1,2-diol in 20 mL pyridine is added 6.66 mL (0.02 mole) oleoyl choride. The reaction mixture is shaken overnight at ambient temperature, filtered, concentrated, and refiltered to afford a yellow oil.

EXAMPLE 3

1,2-Tetradecane di-10-undecenate (also called 1,2-bis-(10-undecenoyloxy)tetradecane), another long chain diol diester of this invention, is prepared in this example.

To a solution of 2.30 g, (0.01 mole) tetradecane-1,2-diol in 20 mL pyridine is added 4.04 g (0.02 mole) 10-undecenoyl chloride. The reaction mixture is shaken at ambient temperature overnight, filtered, concentrated and refiltered to afford an oil.

EXAMPLE 4

1,2-Tetradecane dibromodi-10-undecenate (also called 1,2-bis(9,10-dibromoundecanoyloxy)tetradecane) is prepared in this example.

1,2Bis-(10-undecenoyloxy)-tetradecane (2.0 g, 0.0026 mole, prepared in Example 3) is treated with 5% bromine in carbon tetrachloride (25 mL). After 5 minutes, the volatiles are removed on the rotary evaporator to afford an oil.

Proton NMR spectrum in chloroform-d: chemical shift in ppm (multiplicity, intensity, assignment): 5.08 (apparent octet, 1 H, methine proton), 4.22 (doublet of doublets, 1 H, one half of $CH_2-O_2C$), 4.15 (multiplet, 2 H, CHBr), 4.02 (doublet of doublets, 1 H, one half of $CH_2-O_2C$), 3.85 (doublet of doublets, 2 H, $CH_2Br$), 3.62 (triplet, 2 H, $CH_2Br$), 2.31 (triplet, 4 H, $O_2C-CH_2$), 2.12 (multiplet, 2 H, $CH_2-C-Br$), 1.77 (multiplet, 2 H, $CH_2-C-Br$), 1.3-1.6 (multiplet, 46 H, $CH_2$) and 0.87 (triplet, 3 H, $CH_2$).

EXAMPLE 5

Tetradecane disuccinyloleate (also called 1,2-bis-5-oxa-4-oxotricos-14-enoyloxy)tetradecane) is prepared in this example.

To a solution of 2.30 g (0.01 mole) tetradecane-1,2-diol in 20 mL pyridine is added 7.73 g (0.02 mole) cis-5-oxa-4-oxotricos-14-enoyl chloride. The reaction mixture is shaken at ambient temperature, filtered, concentrated, and refiltered to afford a yellow oil.

EXAMPLE 6

1,2-Tetradecane dimyristate (also called 1,bis(myristoyloxy)tetradecane), another long chain diol diester of this invention, is prepared in this example.

To a solution of tetradecane-1,2-diol (2.30 g, 0.01 mole) in 20 mL pyridine is added myristoyl chloride (4.92 g, 0.02 mole). The reaction mixture is shaken at ambient temperature overnight, filtered, concentrated and refiltered to afford an oil. The oil is taken up in ether and washed with 5% HCl twice, 5% $NaHCO_3$ once, and brine once, dried over sodium sulfate and concentrated on the rotary evaporator (95° C., ca. 100 torr).

EXAMPLE 7

1,2-Hexadecane dioleate (also called 1,2-bis(cis-9-octadecenoyloxy)hexadecane) is prepared in this example.

To a solution of 2.58 g, 0.01 mole) hexadecane-1,2-diol in 20 mL pyridine is added 6.66 mL (0.02 mole) oleoyl chloride. The reaction mixture is shaken at ambient temperature overnight, filtered, concentrated and refiltered to afford an oil.

EXAMPLE 8

1,2-Hexadecane dilaurate (also called 1,2-bis(-dodecanoyloxy)hexadecane) is prepared in this example.

To a solution of 2.58 g (0.01 mole) of 1,2-hexadecanediol in 20 mL pyridine is added 4.38 g (0.02 mole) of lauroyl chloride. The reaction mixture is shaken overnight at ambient temperature, filtered, concentrated and refiltered through silica to afford the title compound.

EXAMPLE 9

1,2-Hexadecane dimyristate (also called 1,2-bis(tetradecanoyloxy)hexadecane) is synthesized in this example.

To a solution of 2.58 g (0.01 mole) of 1,2-hexadecanediol in 20 mL pyridine is added 4.94 g (0.02 mole) of myristoyl chloride. The reaction mixture is shaken overnight at ambient temperature, filtered, concentrated and refiltered through silica to afford the title compound.

EXAMPLE 10

1,2-Hexadecane distearate (also called 1,2-bis (octadecanoyloxy)hexadecane) is prepared in this example.

To a solution of 2.58 g (0.01 mole) of 1,2-hexadecanediol in 20 mL pyridine is added 6.06 g (0.02 mole) of stearoyl chloride. The reaction mixture is shaken overnight at ambient temperature, filtered, concentrated and refiltered through silica to afford the title compound.

EXAMPLE 11

1,2-Hexadecane di-10-undecenate (also called 1,2-bis (10-undecenoyloxy)hexadecane) is prepared in this example.

To a solution of 2.58 g (0.01 mole) of 1,2-hexadecanediol in 20 mL pyridine is added 4.04 g (0.02 mole) of 10-undecenoyl chloride. The reaction mixture is shaken overnight at ambient temperature, filtered, concentrated and refiltered through silica to afford the title compound.

EXAMPLE 12

1,2-Hexadecane dipalmitate (also called 1,bis(hexadecanoyloxy)hexadecane) is prepared in this example.

To a solution of 2.58 g (0.01 mole) of 1,2-hexadecanediol in 20 mL pyridine is added 5.50 g (0.02 mole) of palmitoyl chloride. The reaction mixture is shaken overnight at ambient temperature, filtered, concentrated and refiltered through silica to afford the title compound.

EXAMPLE 13

1,2-Tetradecane dilaurate (also called 1,2-bis (dodecanoyloxy)tetradecane) is synthesized in this example.

To a solution of 2.30 g (0.01 mole) of 1,2-tetradecanediol in 20 mL pyridine is added 4.38 g (0.02 mole) of lauroyl chloride. The reaction mixture is shaken overnight at ambient temperature, filtered, concentrated and refiltered through silica to afford the title compound.

EXAMPLE 14

1,2-Tetradecane distearate (also called 1,2-bis-(octadecanoyloxy)tetradecane), another long chain diol diester of this invention, is prepared in this example.

To a solution of 2.30 g (0.01 mole) of 1,2-tetradecanediol in 20 mL pyridine is added 6.06 g (0.02 mole) of stearoyl chloride. The reaction mixture is shaken overnight at ambient temperature, filtered, concentrated and refiltered through silica to afford the title compound.

EXAMPLE 15

1,2-Tetradecane dipalmitate (also called 1,2-bis (hexadecanoyloxy)tetradecane) is prepared in this example.

To a solution of 2.30 g (0.01 mole) of 1,2-tetradecanediol in 20 mL pyridine is added 5.50 (0.02 mole) of palmitoyl chloride. The reaction mixture is shaken overnight at ambient temperature, filtered, concentrated and refiltered through silica to afford the title compound.

EXAMPLE 16

1,2-Dodecane dimyristate (also called 1,2-bis (tetradecanoyloxy)dodecane) is prepared in this example.

To a solution of 2.02 g (0.01 mole) of 1,2-dodecanediol in 20 mL pyridine is added 4.94 g (0.01 mole) of myristoyl chloride. The reaction mixture is shaken overnight at ambient temperature, filtered, concentrated and refiltered through silica to afford the title compound.

EXAMPLE 17

1,2-Dodecane di-10-undecenate (also called 1,2-bis (10-undecenoyloxy)dodecane) is prepared in this example.

To a solution of 2.02 g (0.01 mole) of 1,2-dodecanediol in 20 mL pyridine is added 4.04 g (0.02 mole) of 10-undecenoyl chloride. The reaction mixture is shaken overnight at ambient temperature, filtered, concentrated and refiltered through silica to afford the title compound.

EXAMPLE 18

Tetradecane dibromooleate (also called 1,2-bis (9,10-dibromooctadecenoyloxy)tetradecane) is prepared in this example.

1,2-bis(cis-9-dibromo-octadecenoyloxy)tetradecane (1.89 g, 0.0025 mole) is treated with a solution of 5 % bromine in carbon tetrachloride (25 mL). After 5 minutes, the volatiles are removed on the rotary evaporator to afford a yellow oil.

EXAMPLE 19

This example outlines the procedure for estimating the in vitro digestibility of the long chain diol diesters of this invention.

Preparation of Reagents and Materials

1. Buffer: A pH 7.1 phosphate buffer is prepared by dissolving 6.8 g. $KH_2PO_4$ in 1 L. of millipore filtered water (to yield 0.05M phosphate). Fifty mg. Ca($NO_3$)$_2$ and 5.0 g. cholic acid (Na salt, an ox bile isolate from Sigma) are added to give 300 microM $Ca^{++}$ and 0.5 % cholic acid in 0.05M phosphate. The pH is adjusted to approximately 7.1 with solid NaOH. Several drops of Baker "Resi-analyzed" toluene are added to prevent bacterial growth during storage at 3°–5° C.

2. Lipase: About 15 mg./mL commercial porcine pancreatic lipase from U.S. Biochemical Corporation is dissolved in buffer.

3. Substrates and Standards: A 1.0 mL volumetric flask is charged with an amount of lipid substrate calculated to give a concentration of 200 nanomoles per microliter in Baker "Resi-analyzed" toluene. (The proper concentration may be approximated by doubling the molecular weight of the lipid in question, dividing by 10, and diluting to the mark; this yields about 200 nanomoles per microliter.) This preparation affords the substrate to be used in the hydrolysis reactions.

Fatty acids and glyceride standards from Nu Chek or Sigma are prepared for elution on thin layer chromatography (TLC) plates (prewashed with 1:1 chloroform/methanol) by diluting the substrate solution with 10:1 toluene (1 part substrate plus 9 parts toluene) in septum vials.

Procedure

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of $CHCl_3:CH_3OH$ and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control, this amounts to 20 nanomoles of substrate spotted on the plate.) Develop with a suitable solvent system, for example, hexane: ethyl ether: acetic acid in a ratio of 60:40:1. After 15 cm elution, dry plate with a heat gun and determine amounts of starting substrate and products of hydrolysis by scanning 10 to 20 nanomoles per channel at a wavelength of 190 nm using a CAMAG TLC Scanner II densitometer equipped with a Spectra Physics 4270 integrator and comparing with controls run at the same time.

Results

Using this procedure and enzyme system, triolein, a triglyceride control, is substantially hydrolyzed in 10 minutes. Under the same conditions, 1,2-tetradecane dioleate, a long chain diol diester of this invention prepared in Example 1, is approximately 20% hydrolyzed in three hours.

EXAMPLE 20

This example illustrates how the novel fat mimetics of this invention are screened for caloric availability by a carefully controlled in vivo animal feeding study.

An experimental relationship between total calories ingested and animal body weight gain is established by monitoring the body weight gain associated with consumption of a nutritionally balanced diet containing varying concentrations of a reference substance such as corn oil which has a known caloric availability. Correlations between total calories ingested and body weight gain are excellent ($r=0.99$).

Caloric availability of an unknown substance is evaluated by substituting a specific weight of the unknown substance for the reference substance and observing the body weight gain. The gain in body weight is equated to a total number of calories using the correlation previously established for the reference data. The estimated number of calories ingested are divided by the weight of unknown substance to give the apparent calories per gram for the unknown substance. Generally speaking, in these bioavailability studies, the degree of perianal pelt soiling correlates with reduced bioavailability.

The test animals are six-week-old male Sprague-Dawley rats obtained from the Portage, Mich. facility of the Charles River Laboratories, Inc. After acclimation for 15 days, the test duration is 14 days. The dietary requirements are established by observing the actual feed consumption of animals provided with unlimited feed. All diets are prepared to contain 50% of the established dietary requirements plus any supplements of reference or unknown substances. In all tests so designed the test animals are maintained in very good health.

The test feeds are AIN-76A and fortified AIN-76A (hereinafter abbreviated "fort") AIN-76A (Teklad). The major components of these diets are as follows:

| component | AIN-76A | fortified AIN-76A |
|---|---|---|
| casein | 20% | 40% |
| corn starch | 15 | 8.08 |
| sucrose | 50 | 26.02 |
| fiber | 5 | 5 |
| corn oil | 5 | 5 |
| AIN mineral mix | 3.5 | 7 |
| AIN vitamin mix | 1 | 2 |
| choline | 0.2 | 0.4 |
| methionine | 0.3 | 0.6 |
| total | 100% | 100% |
| calc. caloric density | 3.85 kcal/gm | 3.9 kcal/gm |

Using these diets supplemented by reference or unknown substances fed as microencapsulated oils, sample body weight (hereinafter abbreviated "wgt") gains for example animals A and B fed corn oil as a reference (9.0 calories/gram) are as follows:

| | Animal A | | Animal B | |
|---|---|---|---|---|
| diet supplied | wgt gain (grams) | calories consumed | wgt gain (grams) | calories consumed |
| ad lib AIN-76A | 73.6 | 1275 | 82.4 | 1370 |
| 50% fort | −3.4 | 651 | −3.8 | 691 |
| 50% fort + 7.75% gelatin | 9.0 | 705 | 8.3 | 747 |
| 50% fort + 7% corn oil | 13.9 | 768 | 15.2 | 831 |
| 50% fort + 14% corn | 28.3 | 913 | 37.9 | 998 |
| 50% fort + 21% corn oil | 57.7 | 1093 | 63.3 | 1183 |

Rats were fed a diet of 50% fort and 21% 1,2-tetradecane dioleate prepared in Example 1 as a test compound under the foregoing procedure, and their weight gain was determined. Based upon the base line control data, and the data from the test compound, it was determined that 1,2-tetradecane dioleate gave about 6.0 kcal/gram upon being metabolized.

EXAMPLE 21

Sweet Chocolate. A low calorie sweet chocolate may be prepared by combining:

| Ingredient | parts |
|---|---|
| Cocoa Powder | 1.0 |
| Sugar | 1.0 |

To this is added a portion of

| | |
|---|---|
| Diol Diester of Example 8 | 1.0 | and the ingredients are mixed thoroughly and passed through a refiner to reduce the particles to desired size. The material is conched, and the remaining diol diester is added. The mixture is poured into molds and quench cooled. No tempering regimen is necessary.

Chocolate Chips. The chocolate prepared above may be melted and deposited into nibs in the usual process.

EXAMPLE 22

Sugar Cookies. Sugar cooks may be prepared by blending:

| Ingredient | parts |
|---|---|
| Sugar | 231 |
| Example 1 Diol Diester | 114 |
| Salt | 3.7 |
| Sodium Bicarbonate | 4.4 |
| Water | 37.4 |
| 5.9% Dextrose Solution (wt/wt) | 58.7 |
| Flour | 391 |

All of the ingredients are creamed together. The dough so formed may be extruded (the dough is very tacky) and baked by the usual process.

EXAMPLE 23

Margarine. Margarine may be prepared by combining the ingredients for the following two phases:

| | parts |
|---|---|
| Oil Phase Ingredients | |
| Example 2 Diol Diester | 59.0 |
| Soybean Hardstock (IV 65) | 40.0 |
| Emulsifier | 1.0 |
| Aqueous Phase Ingredients | |
| Water | 95.8 |

-continued

| Ingredient | parts |
| --- | --- |
| Milk Solids | 2.0 |
| Salt | 2.0 |
| Citric Acid | 0.1 |
| Beta Carotene | 0.1 |

The phases are emulsified in an oil:aqueous phase ratio of 80:20, and passed through a cool scraped surface heat exchanger in the usual process.

EXAMPLE 24

Flavor Bits. Flavor bits for incorporation into baked goods may be prepared by combining the following ingredients:

| Ingredient | parts |
| --- | --- |
| Sucrose | 215 |
| Water | 180 |
| Corn Syrup | 160 |
| Example 23 Margarine | 28 |
| Flavor | 12 |
| Citric Acid | 10 |
| Glycerine | 8 |
| Salt | 5 |
| Dye | 1 |

The first three ingredients are heated to 290° F. and the heat removed. Margarine is mixed in, and the mixture allowed to cool to 160°–170° F. before adding the remaining ingredients. (Almost any flavoring material may be used as flavor, for example, butterscotch or nut.) The mixture is then poured into a cold aluminum pan and frozen in dry ice. The frozen mixture is then cracked and milled into bits.

EXAMPLE 25

Butterscotch Cookies. Butterscotch cookies may be prepared by blending:

| Ingredient | parts |
| --- | --- |
| Flour | 22.0 |
| Example 6 Diol Diester | 20.0 |
| Salt | 0.7 |
| Sodium Bicarbonate | 0.1 |
| Monocalcium Phosphate | 0.1 |
| Vanillin | 0.1 |
| Water | 8.0 | and mixing well. To this is added

| | |
| --- | --- |
| Sugar | 30.0 | which is mixed until dispersed. Then

| | |
| --- | --- |
| Example 25 Butterscotch Bits | 19.0 | are added and mixed until just blended prior to depositing and baking in the usual process.

EXAMPLE 26

Vanilla Wafers. To prepare vanilla wafers, blend:

| Ingredient | parts |
| --- | --- |
| Example 12 Diol Diester | 25 |
| Flour | 100 |
| Granulated Sugar | 72 |
| High Fructose Corn Syrup | 5.0 |
| Nonfat Dry Milk | 1.0 |
| Salt | 1.0 |
| Ammonium Bicarbonate | 0.1 |
| Dried Egg Yolk | 1.0 |
| Water | 55 |

The dough so formed may be rolled, wire cut to ¼ inch thickness, and baked by the usual process to give a vanilla wafer cookie.

EXAMPLE 27

Chocolate Chip Cookies. Chocolate chip cookies may be prepared using the butterscotch cookie recipe of Example 25, but substituting

| Ingredient | parts |
| --- | --- |
| Example 23 Margarine | 10.0 |
| Example 15 Diol Diester | 10.0 | for the fat mimetic ingredient,

| | |
| --- | --- |
| Granulated Sugar | 15.0 |
| Brown Sugar | 15.0 | for the sugar, and

| | |
| --- | --- |
| Example 21 Chocolate Chips | 19.0 | for the butterscotch bits.

EXAMPLE 28

Filled cream. To make a "filled cream" composition, homogenize about

| Ingredient | parts |
| --- | --- |
| Example 3 Diol Diester | 30 |
| Skim Milk | 82 |
| Polysorbate 80 | 0.1 | in a conventional dairy homogenizer.

EXAMPLE 29

Ice Cream. Vanilla ice cream may be prepared by mixing

| Ingredient | parts |
| --- | --- |
| Sugar (10X) | 15.0 |
| Nonfat Dry Milk | 3.9 |
| Salt | 0.4 |
| into Water | 39.0 | for 3 minutes. Then add melted

| | |
| --- | --- |
| Example 8 Diol Diester | 28.4 | and cook to 200° F. while mixing. Hold for 1 minute. Cool to 160° F., and add

| | |
|---|---|
| Sugared Egg Yolks | 12.5 |
| Vanilla Extract | 0.8 | and mix 1 minute. Fill, then cool and freeze.

EXAMPLE 30

Filled Milk. To prepare a 'filled milk' composition, combine about

| Ingredient | parts |
|---|---|
| Example 28 Filled Cream | 100 |
| Skim Milk | 900 | and rehomogenize.

EXAMPLE 31

Cheese Products. To prepare cheese products, treat

Ingredient

Example 30 Filled Milk made with a 1:1 mixture of Examples 10 and 11 long chain diol diesters like natural milk in the normal cheese making process (as is practiced, for example in the production of cheddar or swiss cheese). Preferably add

| | parts |
|---|---|
| Butter Oil | 10 | to the diol diester portion of the filled milk product before it is employed in this process to enhance the proper flavor development of the cheese products.

EXAMPLE 32

Butter Cream Icing. Butter cream icing may be prepared by blending:

| Ingredient | parts |
|---|---|
| Sugar | 227.0 |
| Example 13 Diol Diester | 70.8 |
| Water | 28.4 |
| Nonfat Dry Milk | 14.0 |
| Emulsifier | 1.4 |
| Salt | 1.0 |
| Vanilla | 1.0 |

All of the ingredients are creamed in a mixer at medium speed.

EXAMPLE 33

Crackers. A dough prepared by mixing together

| Ingredient | parts |
|---|---|
| Flour | 100 |
| Sugar | 5.0 |
| Malt | 1.5 |
| Example 17 Diol Diester | 7.5 |
| Salt | 1.0 |
| Sodium Bicarbonate | 0.9 |
| Nonfat Dry Milk | 2.5 |
| High Fructose Corn Syrup | 2.5 |
| Monocalcium Phosphate | 0.75 |
| Water | 28 | is sheeted, stamped, and baked to produce a cracker product.

EXAMPLE 34

Sprayed Crackers. The sheeted and stamped cracker dough of Example 33 may be sprayed with the diol diester of Example 1 after baking.

EXAMPLE 35

Mayonnaise. Mayonnaise can be prepared from the following formulation:

| Ingredient | parts |
|---|---|
| Example 2 Diol Diester | 80 |
| Egg yolk | 5.5 |
| Vinegar | 3.0 |
| Salt | 1.5 |
| Sugar | 2.0 |
| Flavor | 0.5 |
| Water | 7.5 |

The egg yolk is first mixed with the other dry ingredients and a small amount of the water and vinegar in a container. The diester is then slowly poured into the container, while subjecting the container contents to mixing, to form an emulsion. While continuing to agitate the emulsion, the remaining water and vinegar is added.

EXAMPLE 36

Pudding. Pudding can be prepared from the following formulation:

| Ingredient | parts |
|---|---|
| Milk | 67 |
| Sugar | 11 |
| Starch | 5 |
| Water | 9 |
| Flavor | 3 |
| Example 3 Diol Diester | 5 |

The ingredients can be blended together to form a pudding.

EXAMPLE 37

Frying Oil. The diol diester of Example 7 with 1 ppm polydimethylsiloxane may be used for frying food snacks. For frying potatoes, the polydimethylsiloxane may be omitted.

EXAMPLE 38

Pet Food. Dry, expanded animal food kibs may be prepared from the following ingredients:

| Ingredient | parts |
|---|---|
| Hominy Feed | 37 |
| 52% Meat Meal | 17 |
| Wheat Shorts | 13 |
| Example 16 Diol Diester | 16 |
| Corn Germ Meal | 9.6 |
| Wheat Germ Meal | 3 |
| Dried Milk | 0.9 |
| Beet Pulp | 1.7 |
| Fish Scrap | 0.5 |
| Brewer's Yeast | 0.5 |
| Salt | 0.5 |
| Vitamins and Minerals | 0.1 |

The ingredients are mixed together and water added to raise the water content to 27%, before extrusion, pelleting, and drying in the usual manner.

EXAMPLE 39

Semi-Dilute Beverage Clouding Agent Concentrate. A semi-diluted beverage concentrate may be prepared by emulsifying:

| Ingredient | parts |
| --- | --- |
| Water | 63.25 |
| Potassium Sorbate | 0.03 |
| Xanthan Gum | 0.50 |
| Sucrose | 5.25 |
| Citric Acid | 0.024 |
| Polyglycerol Ester | 0.90 |
| Propylene Glycol Ester | 0.90 |
| Diol Diester of Example 4 | 21.8 |
| Diol Diester of Example 9 | 5.4 |
| Milk Protein | 1.9 |
| Powdered Vanilla | 0.15 |
| Flavorings | 0.05 |

The resulting emulsion is a viscous liquid which may be mixed in a ratio of 1.3:1 prior to use as a clouding agent.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. An edible composition comprising, in addition to other edible materials, an edible fat mimetic compound of the formula

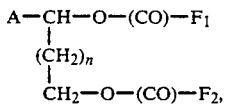

where
A is an aliphatic chain having 7 to 28 carbon atoms, $n = 0$ to 2, and
$F_1$ and $F_2$ are aliphatic groups having 1 to 30 carbon atoms.

2. The composition according to claim 1 wherein $n = 0$, A contains 9 to 28 carbon atoms, and $F_1$ and $F_2$ contain 3 to 23 carbon atoms.

3. The composition according to claim 1 wherein and $n = 1$, A contains 8 to 27 carbon atoms, and $F_1$ and $F_2$ contains 3 to 23 carbon atoms.

4. The composition according to claim 1 wherein $n = 2$, A contains 7 to 26 carbon atoms, and $F_1$ and $F_2$ contains 3 to 23 carbon atoms.

5. The composition according to claim 1 wherein the F groups are derived from fatty acids selected from the group consisting of acetic, propionic, butyric, caproic, caprylic, pelargonic, capric, undecanoic, lauric, myristic, palmitic, stearic, arachidic, behenic, oleic, linoleic, linolenic, eleostearic, and arachidonic acids, and mixtures thereof.

6. The composition according to claim 1 wherein the F groups are derived from an oil selected from the group consisting of non-hydrogenated and hydrogenated soybean, safflower, sunflower, sesame, peanut, corn, olive, rice bran, canola, babassu nut, coconut, palm kernel, cottonseed, palm, and butter oils, and fractions thereof.

7. An edible fat-containing composition comprising, in addition to other edible materials, 11- to 30-carbon aliphatic chains having two vicinal fatty acid ester groups positioned at one terminus, in full or partial replacement of said fat.

8. The composition according to claim 7 wherein the fatty acid ester groups comprise comprise $C_3$ to $C_{23}$ fatty acid ester groups.

9. The composition according to claim 7 wherein the fatty acid ester groups are selected from the group consisting of butyric, caproic, caprylic, pelargonic, capric, undecanoic, lauric, myristic, palmitic, stearic, arachidic, behenic, oleic, linoleic, linolenic, eleostearic, and arachidonic acid ester groups, and mixtures thereof.

10. The composition according to claim 7 the fatty acid ester groups are selected from the group consisting of those derived from non-hydrogenated and hydrogenated soybean, safflower, sunflower, sesame, peanut, corn, olive, rice bran, canola, babassu nut, coconut, palm kernel, cottonseed, palm, and butter oils, and fractions thereof.

11. An edible, fat-containing composition, comprising, in addition to other edible materials, $C_{11}$ to $C_{30}$ diol fatty acid diesters as full or partial fat replacements.

12. The composition according to claim 11 wherein the diols are selected from the group consisting of $C_{11}$ to $C_{20}$ diols having terminal hydroxyl groups.

13. The composition according to claim 11 wherein the fatty acids comprise $C_2$ to $C_{31}$ fatty acids.

14. The composition according to claim 11 wherein the fatty acids are selected from the group consisting of butyric, caproic, caprylic, pelargonic, capric, undecanoic, lauric, myristic, palmitic, stearic, arachidic, behenic, oleic, linoleic, linolenic, eleostearic, and arachidonic acids, and mixtures thereof.

15. The composition according to claim 12 wherein the fatty acids are derived from oils selected from the group consisting of nonhydrogenated and hydrogenated soybean, safflower, sunflower, sesame, peanut, corn, olive, rice bran, canola, babassu nut, coconut, palm kernel, cottonseed, palm, and butter oils, and fractions thereof.

16. A fat-containing food composition comprising food ingredients and 1,2-dodecane, 1,2-tetradecane, or 1,2-hexadecane diol fatty acid diesters as full or partial fat replacements.

17. The composition according to claim 16 wherein the fatty acid diesters comprise those derived from $C_2$ to $C_{31}$ fatty acids.

18. A process for making a fat-containing food composition comprising synthesizing an edible fat product by reacting a diol having 11 to 30 carbons with a fatty acid or a fatty acid derivative selected from the group consisting of a fatty acid, a fatty acid chloride, or a fatty acid methyl ester, admixing the ester thereby produced with a triglyceride oil or another fat mimetic, and incorporating the ester mixture in full or partial replacement of said fat ingredient.

19. The process of claim 18 wherein said diol comprises $C_{11}$ to $C_{20}$ diols and said fatty acids comprise $C_2$ and $C_{31}$ fatty acids.

20. A method for reducing the available calories in a food composition having an edible oil component, which method consists of replacing at least a substantial portion of the edible oil with a $C_{11}$ to $C_{30}$ diol fatty acid diester.

21. The method according to claim 20 wherein said diol comprises $C_{11}$ to $C_{20}$ diols.

22. The method of according to claim 20 wherein the fatty acid diesters comprise $C_3$ to $C_{23}$ fatty acid diesters.

23. The method according to claim 20 wherein said diester is partially digestible.

24. A method of preparing a food composition containing an edible fat ingredient comprising incorporating a compound of the formula

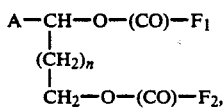

where

A is an aliphatic chain having 7 to 28 carbon atoms, $n = 0$ to 2, and $F_1$ and $F_2$ are aliphatic groups having 1 to 30 carbon atoms, in full or partial replacement of said edible fat ingredient.

25. The method according to claim 24 wherein A has from 9 to 18 carbon atoms and $n = 0$.

26. The method according to claim 24 wherein said F groups are aliphatic groups having 3 to 23 carbon atoms.

27. The method according to claim 24 wherein said food composition comprises a cookie.

28. The method of claim 27 further comprising sugar, salt, sodium bicarbonate, water, and flour.

29. The method of claim 27 wherein said cookie further comprises sugar, flour, salt, monocalcium phosphate, sodium bicarbonate, vanillin, water, margarine and chocolate chips or butterscotch bits.

30. The method of claim 24 wherein said food composition comprises fatty candy.

31. The method of claim 30 wherein said candy is chocolate further comprising cocoa powder and sugar.

32. The method of claim 31 wherein said chocolate is further processed to form chocolate chips.

33. The method of claim 24 wherein said food composition comprises a dairy product.

34. The method of claim 33 wherein said dairy product is selected from the group consisting of filled cream, filled milk, ice cream, and cheese.

35. The method of claim 34 wherein said filled cream and filled milk further comprise skim milk.

36. The method of claim 34 wherein said ice cream further comprises skim milk, sugar, gelatin, flavor and color.

37. The method of claim 24 wherein said food composition is butter cream icing.

38. The method of claim 37 wherein said butter cream icing further comprises sugar, water, non-fat dry milk, emulsifier, salt and vanilla.

39. The method of claim 24 wherein said food composition is a cracker.

40. The method of claim 39 wherein said cracker further comprises flour, sugar, malt, sodium bicarbonate, nonfat dry milk, high fructose corn syrup, monocalcium phosphate and water.

41. The method of claim 24 wherein said food composition is mayonnaise.

42. The method of claim 41 wherein said mayonnaise further comprises egg yolk, vinegar, salt, sugar, flavor, and water.

43. The method of claim 24 wherein said food composition is a pudding.

44. The method of claim 43 wherein said pudding further comprises milk, sugar, starch, water and flavor.

45. The method of claim 24 wherein said food composition is a frying oil.

46. The method of claim 45 wherein said frying oil further comprises polydimethylsiloxane.

47. The method of claim 24 wherein said food composition comprises a pet food.

48. The method of claim 47 wherein said pet food further comprises hominy feed, meat meal, wheat shorts, corn germ meal, wheat germ meal, dried milk, best pulp, brewer's yeast, salt, vitamins and minerals.

49. The method of claim 24 wherein said food composition comprises margarine.

50. The method of claim 49 wherein said margarine further comprises soybean hardstock, emulsifier, water, milk solids, salt, citric acid, and beta carotene.

51. In a food composition having a digestible fat ingredient, an improvement wherein at least a portion of said digestible fat ingredient is replaced by a $C_{11}$ to $C_{20}$ diol terminally esterified fatty acid diester.

52. The improvement according to claim 51 wherein the fatty acids are selected from the group consisting of $C_3$ to $C_{23}$ fatty acids.

53. The improvement according to claim 51 wherein said terminally esterified diol diester delivers 0.5 to 8.5 kcal/gram upon being metabolized.

54. A food composition comprising, in addition to other edible materials, the fatty acid diesters of a terminally esterified $C_{11}$ to $C_{30}$ diol as a low calorie fat ingredient.

* * * * *